(12) United States Patent
Bartyczak et al.

(10) Patent No.: US 8,935,963 B2
(45) Date of Patent: Jan. 20, 2015

(54) GAS GUN FIXTURE TO EVALUATE BLAST WAVE ON TARGET SAMPLE

(75) Inventors: Susan L. Bartyczak, King George, VA (US); Willis Mock, Jr., Fredericksburg, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 368 days.

(21) Appl. No.: 13/507,845

(22) Filed: Jul. 30, 2012

(65) Prior Publication Data

US 2014/0026669 A1    Jan. 30, 2014

(51) Int. Cl.
*G01L 7/00*    (2006.01)
*G01N 3/307*   (2006.01)

(52) U.S. Cl.
CPC .  *G01L 7/00* (2013.01); *G01N 3/307* (2013.01)
USPC .......................................................... 73/756

(58) Field of Classification Search
CPC ................................. G01L 7/00; G01S 15/58
USPC .......................................................... 73/756
See application file for complete search history.

(56) References Cited

U.S. PATENT DOCUMENTS

| | | | | |
|---|---|---|---|---|
| 3,793,874 A | * | 2/1974 | Shockey et al. | 73/12.11 |
| 4,114,510 A | | 9/1978 | Prince et al. | 89/12 |
| 4,349,200 A | * | 9/1982 | Wakefield | 273/371 |
| 5,036,696 A | * | 8/1991 | Ahrens et al. | 73/12.11 |
| 5,714,675 A | * | 2/1998 | Yoshida et al. | 73/12.04 |
| 6,250,198 B1 | * | 6/2001 | Vendetti et al. | 89/44.02 |
| 7,409,848 B2 | * | 8/2008 | Petrinic et al. | 73/12.08 |
| 7,825,850 B2 | * | 11/2010 | Frick | 342/115 |
| 2005/0115316 A1 | * | 6/2005 | Giusti et al. | 73/488 |

OTHER PUBLICATIONS

Bartyczak S. et al.: "Versatile gas gun target assembly for studying ballast wave mitigation in materials", AIP Conf. Proc., 1426, 501 (2012). http://scitation.aip.org/getpdf/servlet/GetPDFServlet?filetype=pdf &id=APCPCS001426000001000501000001&idtype=cvips &doi=10.1063/1.3686327&prog=normal.

* cited by examiner

*Primary Examiner* — Herzon E Williams
*Assistant Examiner* — Mark A Shabman
(74) *Attorney, Agent, or Firm* — Gerhard W. Thielman Esq

(57) ABSTRACT

A test fixture is provided for mounting a sample to a gas gun. The fixture includes a gun barrel mount including an annular enclosure with first and second axial ends, and a sample platform. The mount connects to the gas gun at the first end. The sample platform includes a tubular component having third and fourth axial ends, a pusher disk, an end plate, and a flange. The disk supports the sample and mounts to the end plate. The flange removably attaches to the component at the third end. The end plate removably attaches to the component at the fourth end and to the enclosure at the second end.

4 Claims, 3 Drawing Sheets

GAS GUN FIXTURE TO EVALUATE BLAST WAVE ON TARGET SAMPLE

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to test fixtures for material response to blast waves exposure. In particular, the invention relates to a gas gun barrel attachment to mount a target sample and provide instrumentation for blast measurements.

Traditional methods of measuring blast wave propagation through materials have involved the use of small explosive charges or a gas gun equipped with a Mylar or other burst diaphragm to generate the blast wave and complex target geometries such as instrumented mannequin heads wearing helmets coated with different test materials. There are three key disadvantages to these techniques:

1) explosive charges pose safety and environmental hazards,
2) the repeatability of Mylar burst diaphragms is poor at low pressures (below 100 psi), and
3) complex target geometries introduce uncertainties in the data due to irregular flow of the blast wave around targets and into the interfaces between the helmets and the instrumented mannequin heads.

SUMMARY

Conventional techniques for evaluating material exposure to blast wave yield disadvantages addressed by various exemplary embodiments of the present invention. Various exemplary embodiments provide adaptation to an existing gas gun with components equipped with a fast-opening valve and greatly simplified target geometry. In particular, such embodiments provide a test fixture for mounting a sample to a gas gun. The fixture includes a gun barrel mount including an annular enclosure with first and second axial ends, and a sample platform.

The mount connects to the gas gun at the first end. The sample platform includes a tubular component having third and fourth axial ends, a shock absorption disk and front rear flanges. The disk supports the sample and mounts to the rear flange. The front flange removably attaches to the component at the third end. The rear flange removably attaches to the component at the fourth end as well as to the enclosure at the second end. Other embodiments, alternatively or additionally, provide for pressure gauges for measuring pressure or triggering recordation.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which.

DETAILED DESCRIPTION

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

Exemplary embodiments provide an attachment mechanism for testing blast wave propagation from a conventional gas gun. Coupon samples serving as experimental targets can be installed to test the blast mitigation properties of materials subject to planar blast waves with pressures ranging from 5 psia to 100 psia. The embodiments provide a two-part fixture consisting of a muzzle adapter (FIG. 1) and target assembly (FIG. 2). The muzzle adapter attaches to an existing Ø1.575 inches bore diameter gas gun barrel located in the Shock Physics Facility at Naval Surface Warfare Center (NSWC) Dahlgren Division. Much of this information has been reported in "Versatile Gas Gun Target Assembly for Studying Blast Wave Mitigation in Materials by S. Bartyczak and W. Mock Jr., *AIP Conference Proceedings*, 1426, 501 (2012) available at http://scitation.aip.org/getpdf/servlet/GetPDFServlet?filetype=pdf&id=APCPCS00142600000100050100001&idtype=cvips&doi=10.1063/1.3686327&prog=normal. This document is incorporated herein by reference in its entirety.

Figure 1:
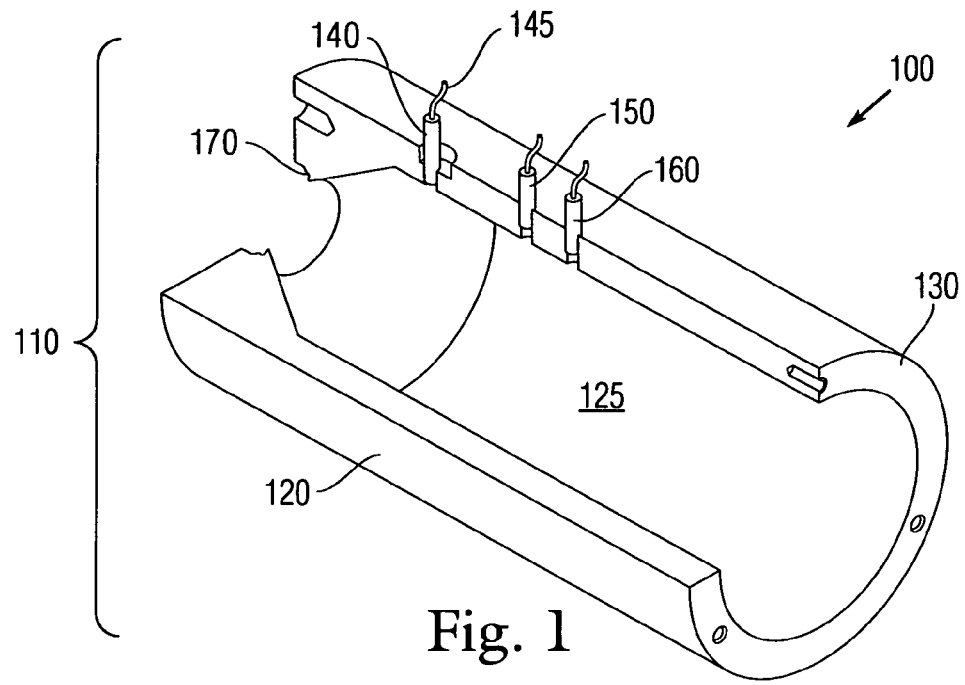
FIG. 1 is an isometric assembly cross-sectional view of a muzzle adapter.
Figure 2:
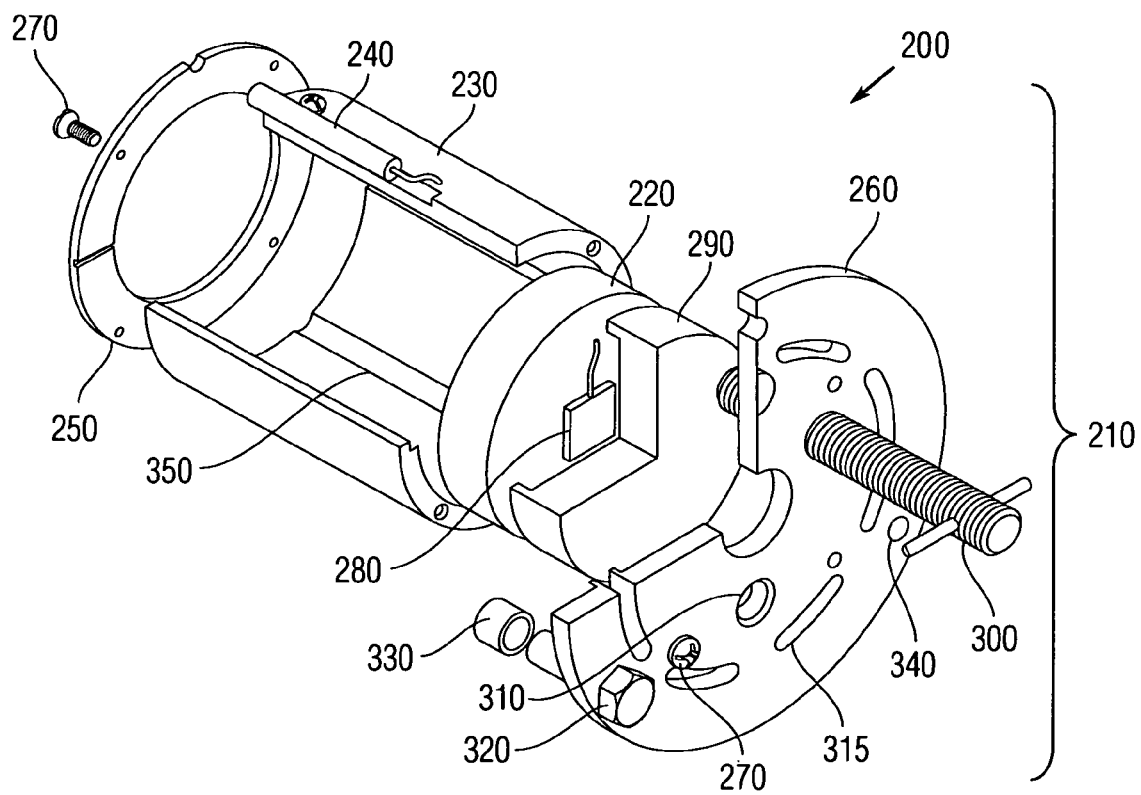
FIG. 2 is an isometric exploded cross-sectional view of the target disposition assembly for mounting a target sample.

FIG. 1 shows an isometric assembly cross-sectional view 100 of a muzzle adapter 110 that includes an annular cylindrical enclosure 120 with inner wall 125. A target assembly attaches to a proximal end 130 of the enclosure 120. The muzzle adapter 110 further includes a triggering pressure gauge PG4 140 using model PCB Piezotronics 132A31 pressure sensor to initiate the oscilloscopes via a communication conduit 145 (such as an electrical conduction wire or cable). The muzzle adapter 110 also includes an instrumentation pair of dynamic pressure gauges PG1 150 and PG2 160 using model PCB Piezotronics 113A31 pressure sensors. A gas gun barrel (not shown) attaches into a recess at a distal (i.e., gun receiving) end 170 of the muzzle adapter.

The muzzle adapter 110 is fabricated from 6061-T6 Al (aluminum alloy), and has a Ø5.5 inches outer diameter and a length of 11.25 inches. The recess at the distal end 170 has dimensions of Ø2.2 inches diameter×0.25 inch deep. The recess includes an O-ring groove Ø1.78 inches inner diameter and Ø2.06 inches outer diameter×0.08 inch deep that contains a Parker 2-134 O-ring to seal the barrel-muzzle adapter joint at the distal end 170 for blast pressure. This distal end 170 of the muzzle adapter 110 includes three ½-13 UNC threaded holes spaced 120° apart on a Ø4.25 inches diameter bolt circle for securing the muzzle adapter 110 to the gun barrel.

The muzzle adapter 110 has a 2.0 inches long transition region with expanding inside diameter to evaluate materials with a diameter larger than the Ø1.575 inch gun bore diameter. A larger target diameter enables maintaining one-dimensional strain conditions in the target center for a longer time before release waves from the target edge reach the center. In this transition region the inside diameter of the muzzle adapter 110 on the distal end 170 increases from Ø1.63 inches to Ø4.25 inches, corresponding to a 33.2° angle. The continuous Ø4.25 inches inner diameter extends to the target assembly end of the muzzle adapter 110 (a distance of 9.0 inches). This proximal end 130 of the muzzle adapter 110 has three ¼-28 UNF threaded holes spaced 120° apart on a Ø4.85 inches diameter bolt circle for securing a target assembly thereto.

The three pressure gauges installed along the enclosure 120 include the triggering transducer gauge 140 and the measurement transducer gauges 150 and 160 for measuring blast wave velocity and pressure as the blast wave propagates towards the mounted target. These gauges are shown disposed 3, 5, and 6 inches, respectively, from the distal end 170 of the muzzle adapter 110. Standard PCB transducer mounting techniques can be used to secure the pressure gauges to the enclosure 120 of the muzzle adapter 110.

FIG. 2 shows an isometric exploded cross-sectional view 200 of the target disposition assembly 210 for attaching a test sample 220. The target assembly 210 includes an annular cylindrical poly(methyl methacrylate) (PMMA) tube 230 and a pressure gauge PG3 240 as a model PCB Piezotronics 113B28 pressure gauge to measure the blast pressure at the target edge. PMMA constitutes a transparent shatter-resistant thermoplastic.

The PMMA tube 230 terminates at a front flange 250 and a rear flange 260. These flanges 250 and 260 attach to the tube 230 by screws 270. The target assembly 210 further includes an accelerometer 280 and a polytetra-fluoroethylene (PTFE) disk 290. The accelerometer 280 represents a model PCB Piezotronics 352C23. PTFE is a synthetic fluoropolymer of tetrafluoro-ethylene. The front flange 250 attaches to the proximal end 130 of the muzzle adapter 110 by the screws 270. PTFE rods 300 connect the rear flange 260 by threaded through-holes 310 to the disk 290. The rear flange 260 also includes arc slots 315.

The rear flange 260 attaches to the muzzle adapter 110 with three steel bolts 320 accompanied by plastic sleeves 330. The bolts 320 insert into through-holes 340. The flanges 250 and 260 are composed of 6061-T6 Al (aluminum alloy) and are secured to the tube 230 with screws 270. The target 220 disposed against the disk 290 for exposure to the blast wave pushes against the front flange 250 by tightening the PTFE rods 300. The front flange 250 includes an annular opening to permit propagation of the blast wave towards the target 220.

Various exemplary embodiments provide an attachment to an existing gas gun to test the blast mitigation properties of materials subject to planar blast waves with pressures ranging from 5 psia to 100 psia. The pressure gauge PG3 240 measures the reflected blast pressure at the target edge. The exemplary embodiments provide a two-part fixture consisting of the muzzle adapter 110 and the target assembly 210. The design of the muzzle adapter 110 includes a tapered transition region that enables the blast wave to expand from the Ø1.575 inches gun bore diameter to Ø4.25 inches and reform into a planar shock front.

The target assembly design 210 includes:
1) attachment points for attaching to the muzzle adapter 110,
2) enables adjustable positioning of the blast face of the target 220 along the axis of the muzzle adapter 110,
3) can accommodate a variety of sample target thicknesses up to 3.5 inches, and
4) includes an instrumentation suite designed to record initial material stress, transmitted material stress, material transit time, reflected blast wave pressure, and target acceleration.

The target assembly 210 includes a PMMA tube 230 with front (blast wave side) and rear 6061-T6 Al flanges 250, 260 that secure to the tube with screws 270. The target to be tested rests against the front flange 250 that is open in the middle to enable the blast wave to impinge directly on the target 220. A PTFE disk 290 with a front recess contacts the back of the target 220 at its edge only. This ensures that the center rear of the target 220 is a free surface.

The PTFE disk 290 is held in position with three PTFE threaded rods 300 that screw into threaded through-holes 310 in the rear flange 260. The threaded rods 300 can be turned by hand, enabling fine-tune adjustment of the pressure that holds the target 220 secure against the front flange 250. This enables a layered target 220 to be tested without necessarily holding the layers together with epoxy.

The target assembly 210 attaches to the muzzle adapter 110 with the three steel bolts 320 that pass through clearance holes at the edge of the rear flange 260. The standoff of the target assembly 210 with respect to the muzzle adapter 110 can be adjusted by using different length bolts 320 with plastic sleeves 330. Using this procedure the position of the target assembly 210 can be easily changed.

The exemplary PMMA tube 230 is 4.5 inches long with a Ø3.0 inches inner diameter and a Ø3.5 inches outer diameter. There is a 0.375 inch gap between the inside diameter of the muzzle adapter 110 and the outside diameter of the tube 230 to permit blast overpressure to escape from the adapter 110. A 0.085 inch deep half-moon slot in the outer wall of the tube 230 is used to hold the pressure gauge PG3 240 flush with the front flange 250. Several longitudinal grooves 350 in the inside wall of the tube 230 enable the wires of thin film gauges or other instruments to pass through that may (in alternate embodiments) be placed in front of and/or behind the target 220. These and other dimensions represent exemplary values and artisans of ordinary skill will recognize that they are not limiting.

The 0.125 inch thick front flange 250 has a Ø3.5 inches outer diameter, a Ø2.5 inches inner diameter, and four clearance holes spaced 90° apart on a Ø3.25 inches diameter bolt circle for 2-56 UNC screws to attach the flange 250 to the PMMA tube 230. This tube 230 rests in a 0.1 inch deep recess in the rear flange 260 and is secured with four 6-32 UNC screws spaced 90° apart on a Ø3.25 inches diameter bolt circle.

Six 0.19 inch wide slots on a Ø3.88 inch diameter circle in the rear flange 260 ensure release of the blast wave. The three 6-inch long by ½-13 UNC PTFE threaded rods 300 screw into threaded holes 310 spaced 120° apart on a Ø2.28 inches diameter bolt circle in the rear flange 260. The 0.75 inch thick by Ø3.0 inches diameter PTFE target backup disk 290 has a Ø2.5 inches diameter by 0.125 inch deep recess that contains the accelerometer 280 for measuring the acceleration of the target system due to the blast wave. These dimensions are merely exemplary, and artisans of ordinary skill will recognize that the components described herein can be scaled larger or smaller depending on the target 220 and its test conditions.

The firing event begins when the fast-acting ball valve in the gas gun is opened, releasing high pressure gas from the gun breech. The released gas forms a planar blast wave that travels down the Ø1.575 inch bore diameter barrel until it reaches the distal end 170. A 2.0 inches long transition region in the muzzle adapter 110 causes the blast wave to expand to Ø4.25 inches diameter, slightly larger than the diameter of the target 220 to permit the gas to escape.

This expansion of the blast wave causes turbulence in the flow of the blast pressure. The Ø4.25 inches bore in the muzzle adapter 110 is 9.0 inches long to enable the turbulence to subside and the planar blast wave to reform prior to impact with the target assembly 210. The position of the target assembly 210 can be adjusted along the length of the muzzle adapter 110 in order to tailor its location for optimum flow characteristics.

The muzzle adapter 110 is equipped with a trigger gauge 140 to start the data acquisition system and two pressure gauges, PG1 150 and PG2 160 to record incident pressure and velocity of the blast wave prior to impact with the target assembly. The target assembly 210 is equipped with one pressure gauge PG3 240 to record reflected pressure and an accelerometer 280 to record acceleration of the test sample 220. As the blast wave impacts the target assembly 210, its pressure front expands around the target 220 and escapes through a 0.375 inch gap between the target assembly 210 and the muzzle adapter 110.

Figure 3:
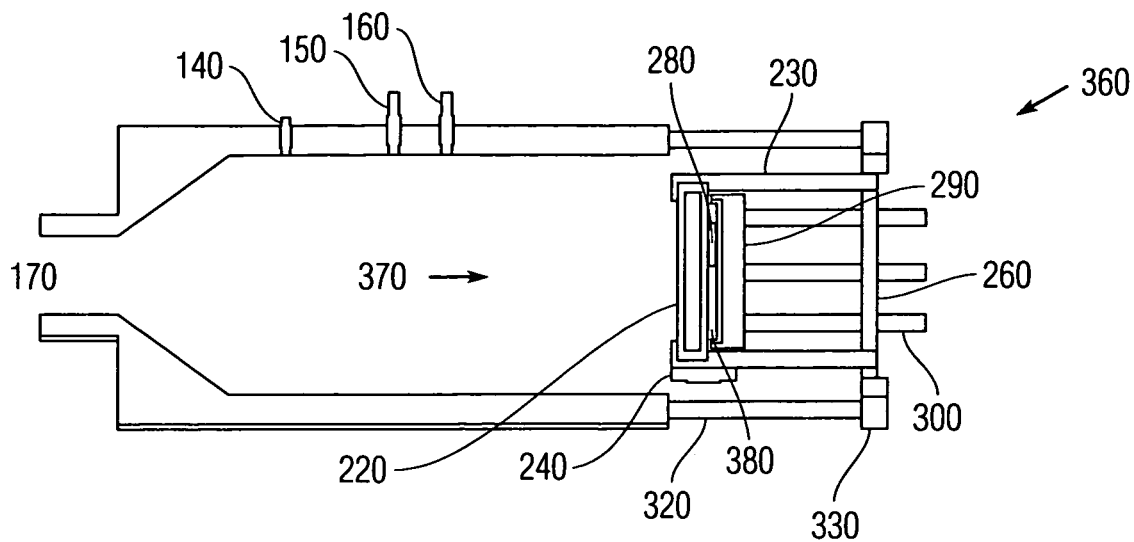
FIG. 3 is an elevation assembly view of the muzzle adapter and target assembly.

FIG. 3 shows an elevation schematic view 360 of an experimental setup with the muzzle adapter 110 and target assembly 210 connected together for investigating blast wave reduction in a layered target system. The blast wave propagates in a direction 370 from the distal end 170 towards the target 220. The gauges PG1 150 and PG2 160 measure the blast wave velocity along direction 370 and accompanying pressure. The target 220 and the disk 290 are separated by a thin air gap 380. The gauge PG3 240 measures the reflected blast pressure at the exposed face of the target 220. The accelerometer 280 on the rear of the target 220 measures the damped vibration of the target assembly 210.

Figure 4:
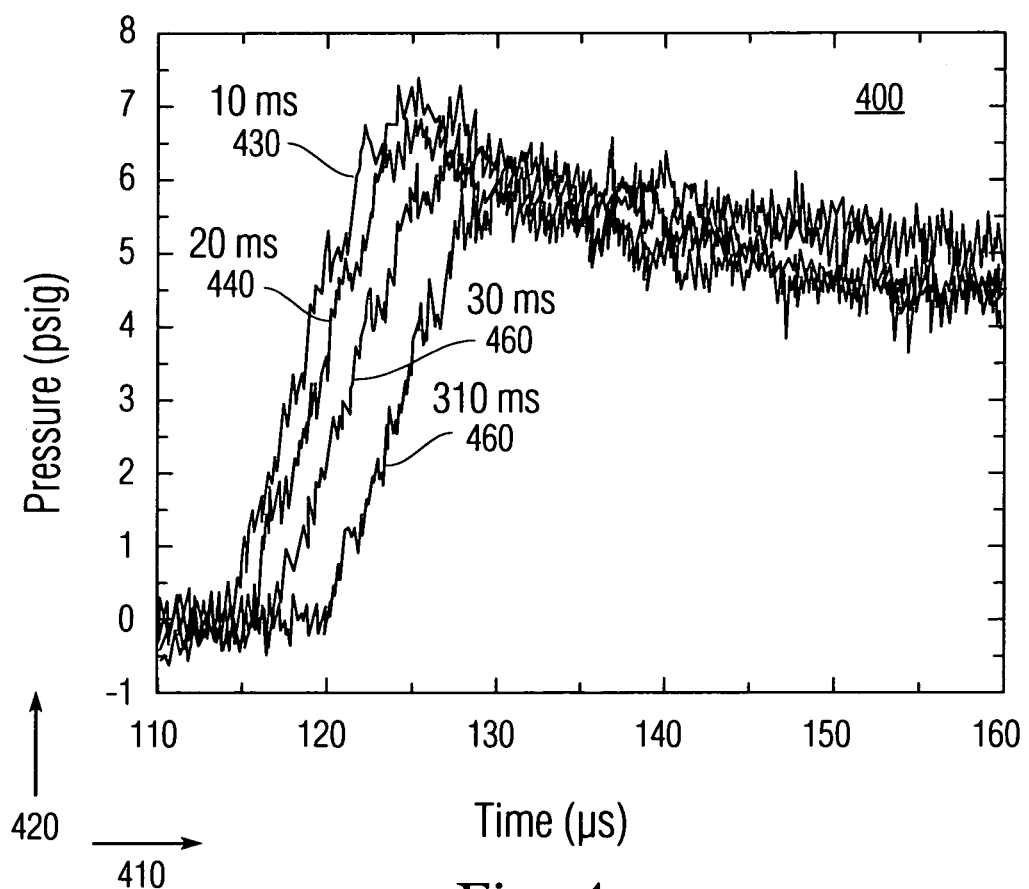
FIG. 4 is a graphical view of pressure response to valve opening.

Initially a series of checkout experiments was conducted without a target assembly 210 to determine the largest ball valve opening time without reducing the blast pressure appreciably. FIG. 4 shows a graphical view 400 of several transient pressure profiles. The abscissa 410 represents time in microseconds (μs) and the ordinate 420 represents blast pressure in psig. The time is recorded with respect to initiation from the trigger gauge 140. The pressure responses for gauge PG1 150 are plotted for valve opening times: 10 ms as line 430, 20 ms as line 440, 30 ms as line 450 and 310 ms as line 460.

For a very long valve opening time (on the order of many hundreds of milliseconds), the compression wave in the gun barrel would not be expected to form into a blast wave at the target 220. For these tests, the blast pressure was measured with gauge PG1 150 for selected valve opening times for a 60 psig breech pressure. As the valve opening time increases, the blast wave slope, amplitude, and velocity decrease. Based on these results a 20 ms valve opening time 440 was chosen for the blast wave experiments since the 10 ns and 20 ms profiles, 430 and 440 respectively, are very similar.

A series of experiments was subsequently performed to determine blast wave planarity for different target standoff positions in the muzzle adapter 110. For these experiments, the target 220 was removed, and a supplemental pressure gauge PG4 (not shown) was mounted in the middle of a modified PTFE backup disk 290 such that this gauge was in the same plane as gauge PG3 240. To determine blast wave planarity, the arrival time of the blast wave at this gauge PG4 was compared to that of gauge PG3 240 for selected standoff positions of the rear flange 260 from the proximal end 130 of the muzzle adapter 110. At 0 mm standoff, the rear target flange 260 attaches directly to the rear of the muzzle adapter 110. In this position, the blast wave releases through the arc slots 315 in the rear target flange 260. At this standoff position, the front of the target 220 was disposed 19 mm from gauge PG2 160.

At 115 mm standoff the front of the target 220 is flush with the proximal end 130 of the muzzle adapter 110. In this configuration, long bolts 320 with plastic sleeves 330 are used to stand off the rear target flange 260 a distance of 115 mm from the distal end 130 of the muzzle adapter 110. The blast wave planarity experiments were performed for 60 psig breech pressure. Satisfactory blast wave planarity was achieved for the 115 mm standoff position. In this position, the blast wave arrived at gauge PG4 about 1 μs prior to arriving at transducer gauge PG3 240. The measured blast wave velocity was 397 m/s (1302 ft/s) for this test.

After performing the impact planarity experiments, layered target experiments were conducted for a breech pressure at 60 psig. The layered target 220 consists of a 3.18 mm thick Sorbothane disk (50 durometer, shore 00) sandwiched between two 3.1 mm thick 6061-T6 Al coupons. Sorbothane is a commercially available synthetic viscoelastic polymer used for shock attenuation and vibration isolation. For these tests, the Sorbothane material was covered with the aluminum coupons to preclude or mitigate non-uniform deformation under blast. The aluminum coupons consist of 2.3 mm and 0.8 mm thick aluminum disks with a polyvinylidene fluoride (PVDF) thin film polymer stress gauge (not shown) between them. The PVDF gauges from Dynasen, Inc. of Goleta, Calif. measure the input and output stresses in the sample material of the target 220.

Figure 5:
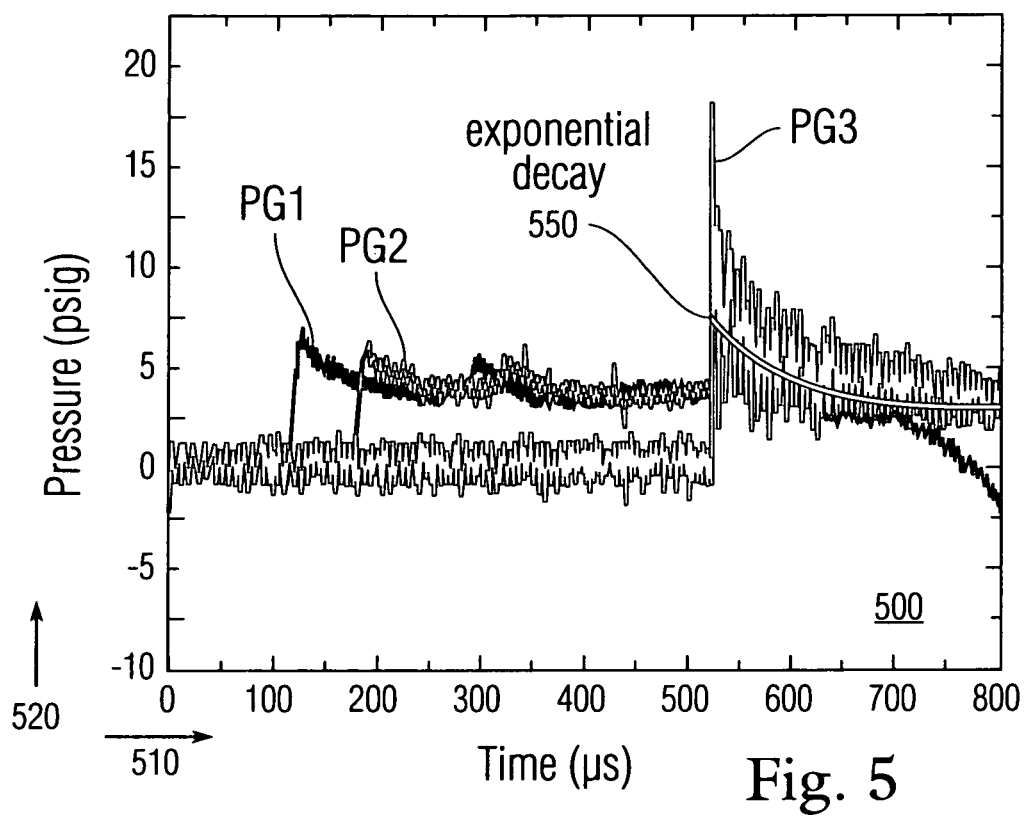
FIG. 5 is a graphical view of a pressure blast propagation.

FIG. 5 shows a graphical view 500 of pressure-time profiles for a selected experiment. The abscissa 510 represents time in microseconds (μs) and the ordinate 520 represents pressure in psig. Measurement lines for gauges PG1, PG2 and PG3 are shown, with an exponential decay trace 530 being highlighted for gauge PG3 240 beginning at 520 μs. Time is measured with respect to the trigger pulse as determined by the trigger gauge 140. The breech pressure within the enclosure 120 was 60 psig for these experiments. The incident peak pressures measured by respective gauges PG 1 150 and PG2 160 are 7.0 psig and 6.1 psig. A 403 m/s (1322 ft/s) blast wave velocity was calculated using these profiles. The gauge PG3 240 measures a 7.7 psig exponential decaying reflected blast wave with a 250 μs duration.

Figure 6:
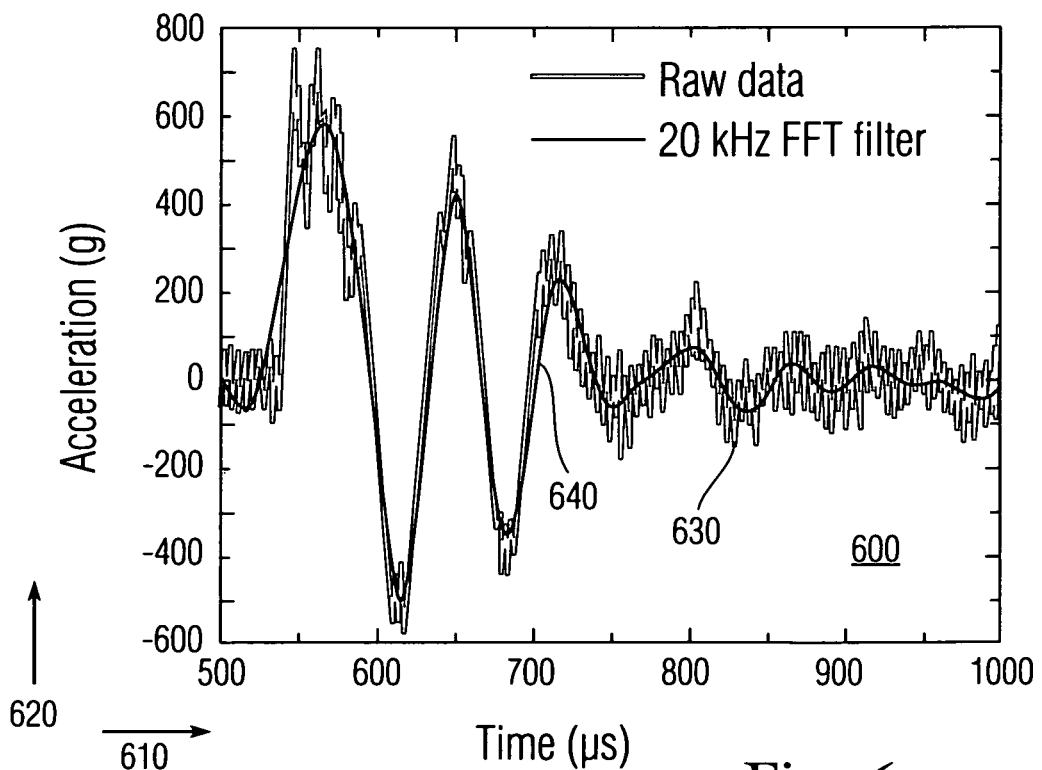
FIG. 6 is a graphical view of acceleration results.

FIG. 6 shows a graphical view 600 of acceleration-time profiles for the accelerometer 280 for selected valve opening times. The abscissa 610 represents time in microseconds (μs) and the ordinate 620 represents acceleration in equivalent earth gravitational acceleration at sea-level. The accelerometer 280 measures the damped vibration of the natural frequency of the target system.

A damping coefficient of 0.074 (using the first two periods of the plot) was calculated from these data. The damped natural frequency of the system was 12 kHz (83 μs period). For the purposes of analysis, the target 220 responds to a long-duration pulse as measured by the gauge PG3 240 due to the 250 μs blast pulse duration being three times the 83 μs system period. Because the damping coefficient varies between zero and unity, this result suggests that minimum damping is achieved with this target configuration and low (7.7 psig) reflected pressure. A damping coefficient can be obtained for the system from this damped sinusoidal vibration. Time is measured with respect to the trigger pulse as determined by the trigger gauge 140.

Due to the recent conflicts in the Middle East and the threat of improvised explosive devices (IEDs), the incidence of blast related injuries is increasing as is the need for research to develop blast mitigating materials. Various exemplary embodiments have the potential to be used commercially by other facilities using gas guns to characterize blast wave attenuation of the new materials developed.

The purpose of various exemplary embodiments is to provide a capability for using an existing gas gun to test the blast mitigation properties of materials with the end goal of identifying materials suitable for military armor to protect warfighters from blast-related injuries. The advantages of various exemplary embodiments include:

1) the design adapts to an existing gas gun that uses a fast-opening valve and non-explosive nitrogen and helium gases to generate the blast wave thereby eliminating the safety and environmental hazards associated explosive charges and the poor repeatability issues associated Mylar burst diaphragms, 2) a unique target assembly design that enables: a) a test sample 220 to be located at any position in the muzzle adapter 110 in a continuous manner by simple screw adjustment, b) test samples 220 of different thicknesses to be easily inserted into the target assembly 210 for measurement, and c) a sandwich test sample target 220 to be held together in the target assembly 210 by simple screw adjustment.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A test fixture for mounting a sample to a gas gun, said fixture comprising:

a gun muzzle mount including an annular enclosure with first and second axial ends, said mount connecting to the gas gun at said first end, wherein said mount further includes:

a first pressure gauge to measure dynamic internal pressure of said enclosure between said first and second ends; and a second pressure gauge to trigger recordation of measurements from said first pressure gauge; and a sample platform including a tubular component having third and fourth axial ends, a shock absorption disk, and front and rear flanges, wherein said disk supports the sample and mounts to said rear flange, said front flange removably attaches to said component at said third end, said rear flange removably attaches to said component at said fourth end and to said enclosure at said second end.

2. The fixture according to claim 1, wherein said platform further comprises:

a third pressure gauge to measure blast pressure adjacent the sample.

3. The fixture according to claim 1, wherein said platform further comprises:

an accelerometer being attached to the sample disposed within a recess of said disk.

4. The fixture according to claim 1, wherein said rear flange attaches to said disk by a plurality of threaded rods.

* * * * *